United States Patent
Bougaret et al.

[11] Patent Number: 5,334,393
[45] Date of Patent: Aug. 2, 1994

[54] SUSTAINED-RELEASE TABLET BASED ON ISOSORBIDE 5-MONONITRATE AND PROCESS FOR PREPARING IT

[75] Inventors: Joël Bougaret, Castres; Michel Sournac, Dijon, both of France

[73] Assignee: Pierre Fabre Medicament, Boulogne, France

[21] Appl. No.: 756,810

[22] Filed: Sep. 9, 1991

[30] Foreign Application Priority Data

Sep. 7, 1990 [FR] France ............................. 90 11133

[51] Int. Cl.$^5$ ................................................. A61K 9/20
[52] U.S. Cl. ..................................... 424/469; 424/468; 424/464; 424/470
[58] Field of Search ............... 424/464, 468, 469, 470, 424/484

[56] References Cited
FOREIGN PATENT DOCUMENTS 0219161  4/1987  European Pat. Off. .
3328894  3/1985  Fed. Rep. of Germany .
0299877  1/1989  France .
2181052  4/1987  United Kingdom .

OTHER PUBLICATIONS

Budavari et al. (1989), The Merck Index, p. 5120.
Gennaro (1985) Remington's Pharmaceutical Sciences, Mack Pub., p. 853.

Primary Examiner—Thurman K. Page
Assistant Examiner—Raj Bawa
Attorney, Agent, or Firm—Dressler, Goldsmith, Shore & Milnamow, Ltd.

[57] ABSTRACT

The present invention relates to a sustained-release tablet, characterized in that it comprises as active principle isosorbide 5-mononitrate (5-ISMN) in the form of a powder having a particle size of 80 μm to 500 μm, in homogeneous dispersion in a hydrophilic matrix based on at least one swelling component and at least one diluent component.

14 Claims, 4 Drawing Sheets

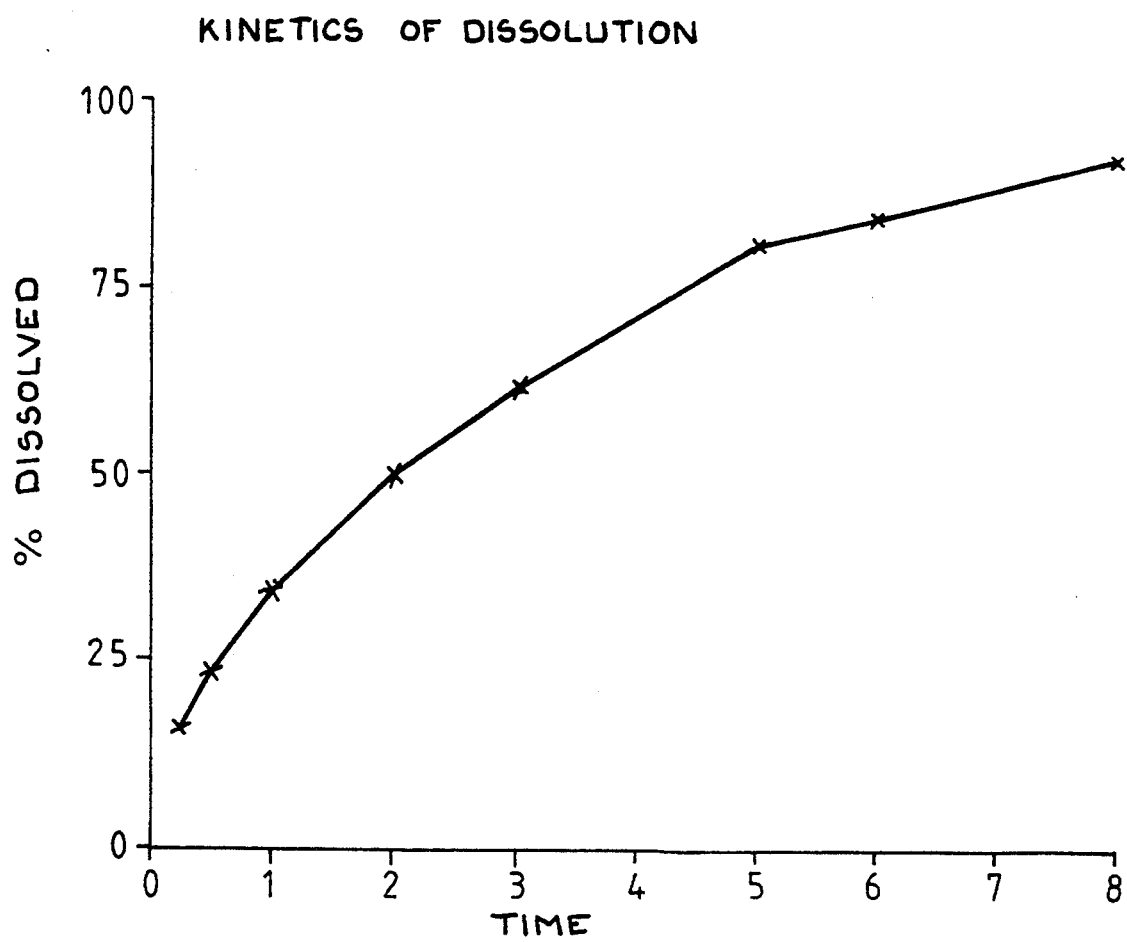
FIG_1

FIG_2
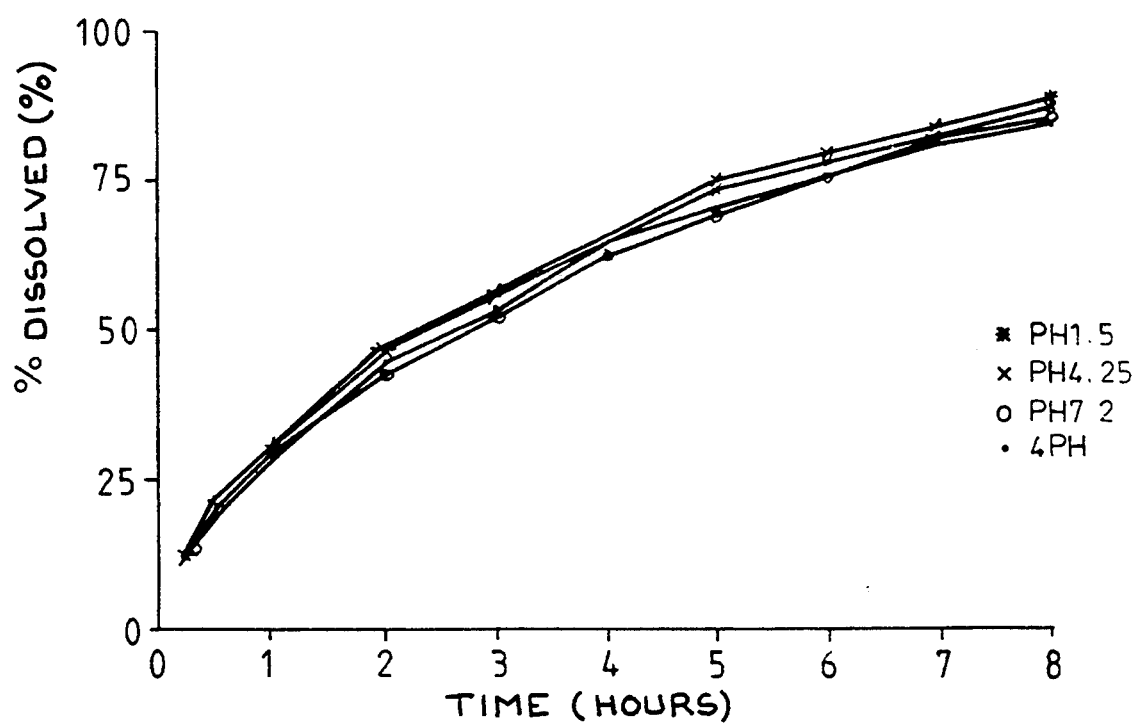

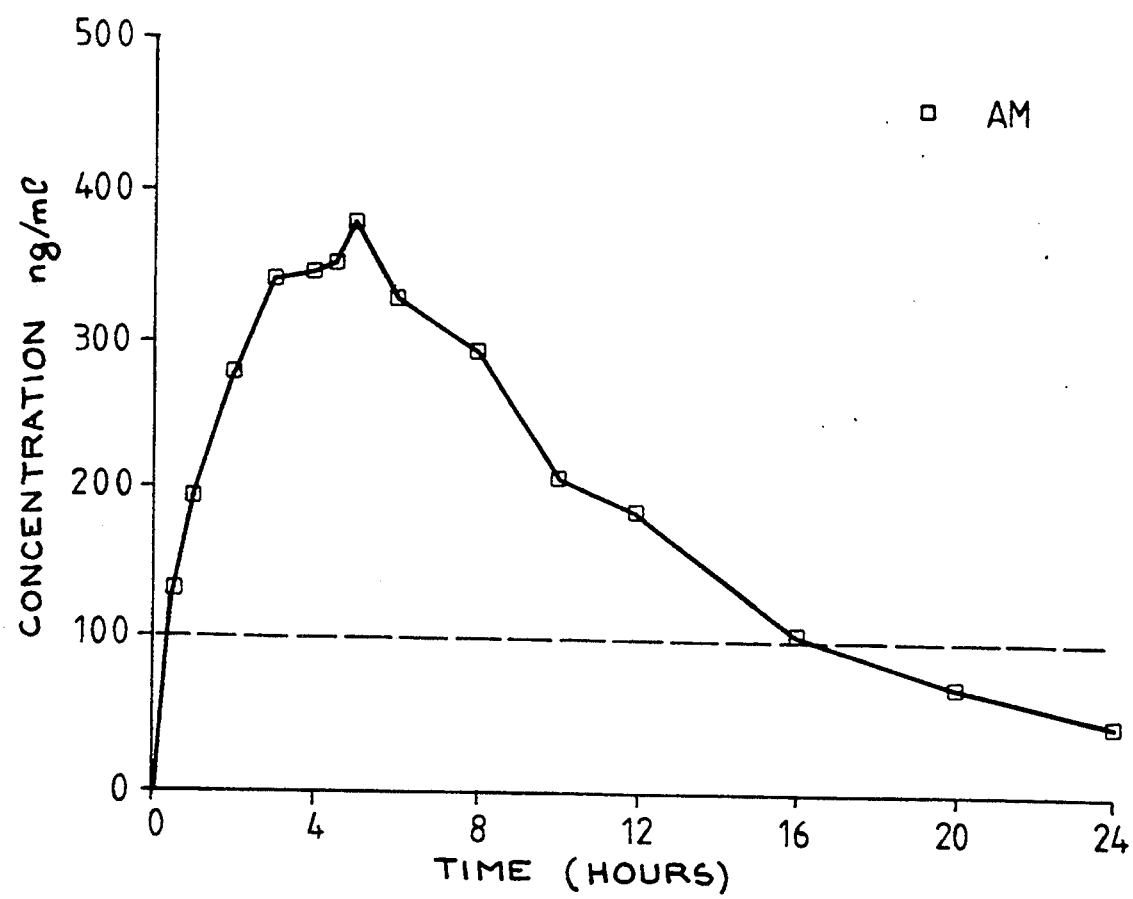
FIG_3

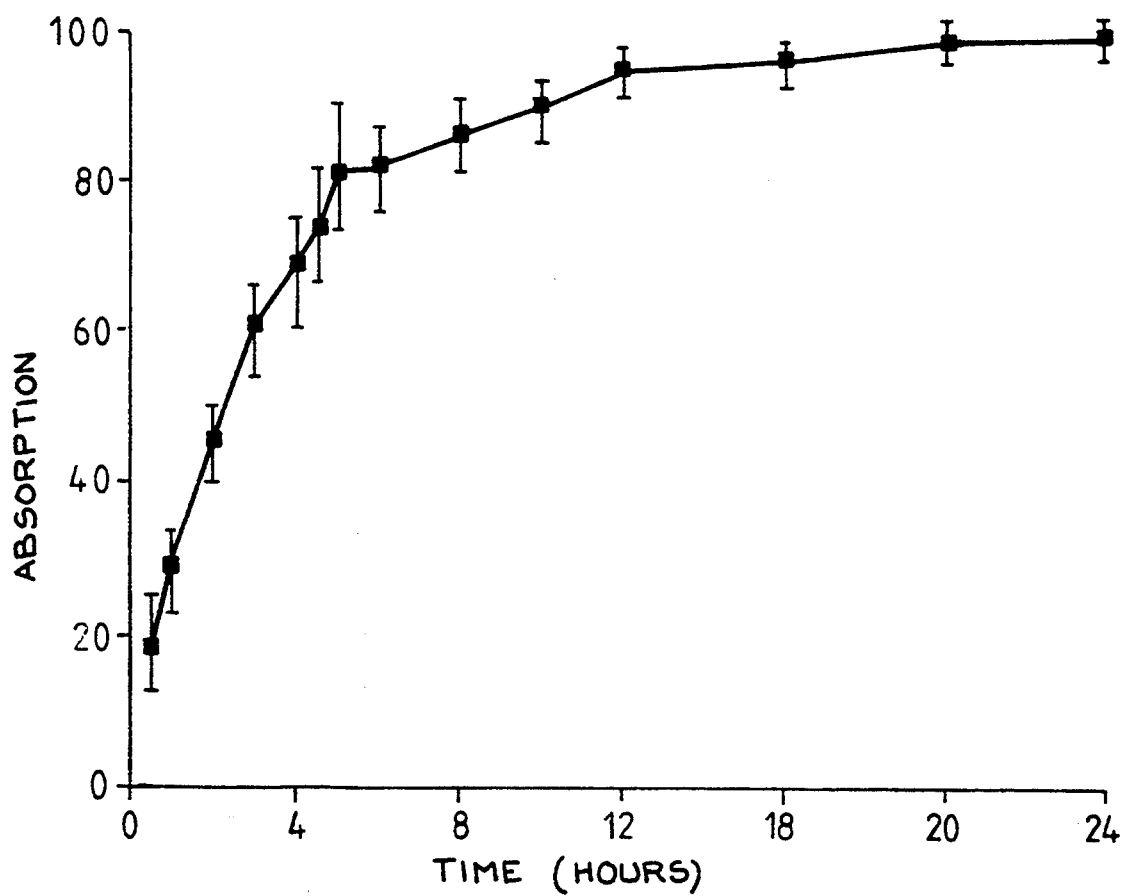
FIG_4

SUSTAINED-RELEASE TABLET BASED ON ISOSORBIDE 5-MONONITRATE AND PROCESS FOR PREPARING IT

The present invention relates to a pharmaceutical composition based on isosorbide 5-mononitrate, and having a dosage form which is suitable for prolonged release of this active principle over time.

Isosorbide 5-mononitrate (5-ISMN), an active metabolite of ISDN, is the first representative of a new generation of nitrated vasodilators. It permits an effective preventive treatment of anginal disease, and the absence of a hepatic first-pass effect endows it with advantageous properties in cardiac insufficiency.

However, 5-ISMN has drawbacks which make it difficult to prepare it in a sustained-release dosage form, namely:

a static electricity phenomenon, which makes any dry mixing almost impossible as a result of a virtually zero flowability, a sublimation phenomenon on exposure of 5-ISMN to particular stress conditions (60° C.–75% relative humidity), and a very high solubility of 5-ISMN in water and buffer solutions, which makes it difficult to control the release of the active principle from the dosage form.

The object of the present invention is to develop a suitable dosage form of 5-ISMN enabling the above-mentioned drawbacks to be eliminated.

Thus, it was demonstrated that a well-defined particle size fraction of 5-ISMN in the form of a powder had the appropriate qualities for such a formulation, namely a low level of electrostatic phenomena, a far less marked tendency to sublime and qualities of flowability and compressibility.

More specifically, the present invention relates to a tablet, characterized in that it comprises as active principle isosorbide 5-mononitrate (5-ISMN) in the form of a powder of particle size 80 $\mu$m to 500 $\mu$m, determined by the air-Jet sieve method, in homogeneous dispersion in a hydrophilic matrix based on at least one swelling component and at least one diluent component.

The use of a powder of such particle size, namely having particles between 80 $\mu$m and 500 $\mu$m in size, and preferably having 70% of these particles between 80 $\mu$m and approximately 250 $\mu$m in size, has, moreover, a further advantage. It makes it possible to avoid the use, during the manufacture of said composition, of the wet granulation technique which is a common method but one which has drawbacks.

The air-Jet sieve method used according to the invention to define the particle size of the 5-ISMN is a technique widely used by those skilled in the art on account of its great sensitivity and reliability, and is consequently very familiar to them. The operating conditions employed in the context of the invention will be clarified in greater detail below.

The preferred particle size profile for the 5-ISMN according to the invention and determined according to this technique corresponds to approximately:

40 to 60% of 5-ISMN of particle size larger than 80 $\mu$m and smaller than 100 $\mu$m, 20 to 50% of 5-ISMN larger than 100 $\mu$m and smaller than 250 $\mu$m, approximately 5% of 5-ISMN larger than 250 $\mu$m and smaller than 500 $\mu$m, and approximately 0.5% of particle size larger than 500 $\mu$m, the residue consisting of 5-ISMN having a particle size smaller than 80 $\mu$m.

As regards the hydrophilic matrix, this comprises at least one swelling component and one diluent component in a swelling/diluent weight ratio of between 0.2 and 0.7, and preferably equal to 0.5.

The diluent component (diluent) contains at least one intrinsic diluent and one thickening diluent, in a thickening diluent/diluents ratio of between 0.1 and 0.6, and preferably equal to 0.3.

This combination makes it possible to stabilize the in vitro release of the 5-ISMN essentially during the terminal stage of the two-phase release.

According to the present invention, the intrinsic diluent is preferably chosen from one or more substances comprising lactose, sorbitol, mannitol, calcium phosphate or sulfate, colloidal silica and/or microcrystalline cellulose. On the other hand, this intrinsic diluent may not be chosen from polyvinylpyrrolidone and the close derivatives thereof.

The thickening diluent (thickener) is preferably chosen from one or more substances comprising starches, starch derivatives, microfine cellulose, xanthan gums, natural or semi-synthetic, and/or dextrins.

As regards the swelling component (swelling agent), this is preferably chosen from one or more hydrophilic polymeric substances of apparent viscosity, at a concentration of 2% by weight relative to the weight at 20° C., between 0.1 Pa.s and 100 Pa.s. These hydrophilic polymer substances are preferably chosen from the family of proteinaceous or cellulosic hydrocolloids, and in particular from alginic derivatives, methylcellulose, carboxymethylcellulose, hydroxypropylcellulose and/or methylhydroxypropylcellulose. Preferably, methylhydroxypropylcellulose of viscosity in the region of 15 Pa.s will be used.

These polymers may be used alone or in combination with one another.

As a result of the intrinsic qualities of the 5-ISMN thus selected and the characteristics of the hydrophilic matrix form used, a dosage form having excellent cohesion and characterized by two-phase and pH-independent kinetics of release in vitro is thereby obtained.

The tablets thereby obtained contain from 5% to 20% by weight of active principle relative to the total weight of the tablet. This content will preferably be equal to approximately 10% by weight of the active principle relative to the total weight of the tablet.

Finally, according to a preferred embodiment, an aqueous film-coating, preferably based on compatible cellulose derivatives of the hydroxypropylcellulose or methylhydroxypropylcellulose type, with the addition, where appropriate, of a plasticizer of the glycerin and/or polyethylene glycol type, is applied to the matrix base described above.

This film-coating of hydrophilic matrices using an aqueous solvent proves to meet the requirements of maintenance of resistance to crushing without significant modification of the profile of release.

This same film-coating can naturally be colored by the addition of pigment suspensions prepared at the time of use.

The tablets according to the invention may also contain a lubricant such as stearic acid or derivatives, and/or a colorant, preferably pink in color, in the form of a synthetic organic shellac, for example erythrosine shellac.

The present invention also relates to a process for manufacturing said tablets, characterized in that:
the various swelling and diluent components and the active principle are sieved and then mixed;
a lubricant and, where appropriate, other additives is-/are added to the mixture thereby obtained;
this final mixture is then tableted and, where appropriate,
film-coating of said tablet thereby obtained is performed.

The tablets thereby obtained may be oval in shape and optionally divisible.

Such a dosage formulation of isosorbide 5-mononitrate hence has the advantages of reducing the number of daily doses, of decreasing the side effects characteristic of nitrated derivatives and which are linked to excessively high plasma concentrations, and consequently of obtaining a mean plasma level which is stable over several hours after administration. A tablet based on isosorbide 5-mononitrate according to the invention hence enables a sustained and regular release of this active principle to be secured over a time period of approximately 6 to 18 hours.

The tablets obtained according to the invention are especially useful for the treatment of anginal disease and cardiac insufficiency.

The examples and figures given below without implied limitation will enable other advantages and characteristics of the present invention to be demonstrated.

FIG. 1 shows the kinetics of release of 5-ISMN contained in a composition according to the invention, in vitro as a function of time.

FIG. 2 shows the kinetics of release of 5-ISMN contained in a tablet according to the invention, in vitro as a function of different pH values.

FIG. 3 shows the mean curve for the plasma 5-ISMN levels obtained after administration of the compound in the form of tablets according to the invention.

FIG. 4 shows the mean curve for the percentages of 5-ISMN absorbed.

EXAMPLE 1

Formulation of tablets according to the invention

|  | Tablet No. | | | | |
|---|---|---|---|---|---|
|  | 1 | 2 | 3 | 4 | 5 |
| Isosorbide 5-mononitrate | 50.0 | 40.0 | 20.0 | 80.0 | 60.0 |
| Lactose | 140.0 | 170.0 | 60.0 | 200.0 | 200.0 |
| Mannitol | 50.0 | | | | |
| Corn starch, pregelatinized | | 69.0 | 50.0 | | 75.0 |
| Xanthan gum | 60.0 | | | 100.0 | |
| MHPC 4 Pa.s | | | 20.0 | | |
| MHPC 15 Pa.s | 107.0 | 115.0 | 40.0 | 150.0 | 100.0 |
| Magnesium stearate | 4.35 | 3.88 | 2.6 | 4.45 | 4 |
| Colloidal silica, anhydrous | 2.5 | 2.0 | 1.34 | 2.35 | 2.5 |
| Erythrosine shellac E 127 | 0.15 | 0.12 | 0.06 | 0.2 | |
| Intermediate Unit Mass | 414.0 | 400.0 | 194.0 | 537.0 | 441.5 |
| MHPC, partially substituted | 13.95 | 13.955 | 5.975 | 11.65 | |
| Polyoxyl 8 stearate | | | | | |
| Sodium lauryl sulfate | 0.05 | 0.045 | 0.025 | 0.05 | |
| Glycerin Codex | 2.0 | 2.0 | 1.0 | 2.3 | |
| Final Unit Mass | 430.0 | 416.0 | 201.0 | 551.0 | 441.5 |

EXAMPLE 2

Characterization of the particle size of the 5-ISMN used according to the invention by the air-jet sieve, type ALPIN JET SIEVE, method Operating conditions 20 g sample,
350 g (sic) partial air vacuum,
time 4 min from 80 to 100 μm, then 3 mm (sic) from 250 to 500 μm.

Under these conditions, three batches of 5-ISMN, A, B and C, were tested. The results are presented in the following table:

| Desired profile | | A % | B % | C % |
|---|---|---|---|---|
| 80 μm | 40 ≦ ≦ 60 | 47.5 | 48.2 | 49.2 |
| 100 μm | 20 ≦ ≦ 50 | 26 | 34.4 | 34.85 |
| 250 μm | ≦ 5 | 0.0 | 0.9 | 0.0 |
| 500 μm | ≦ 0.5 | 0.0 | 0.0 | 0.0 |

These three batches clearly have the desired particle size profile.

EXAMPLE 3

Kinetics of release in vitro

The study of the changes in the percentage of 5-ISMN dissolved was performed as a function of time. This test was carried out using a rotating paddle apparatus (100 rpm/900 ml of water). The results obtained are as follows, and are shown in FIG. 1:

% dissolved at 0.25 hour : 5% to 20%,
% dissolved at 1 hour : 20% to 40%
% dissolved at 4 hours: 60% to 80%
% dissolved at 8 hours: ≧80%

EXAMPLE 4

Kinetics of release of the active principle in vitro as a function of pH

This study was carried out at pH values of 1.5, 4.25 and 7.2 and variable values. The results obtained are shown in FIG. 2.

The three kinetic profiles of release at constant pH do not differ significantly from one another. As regards the dissolution profile obtained at variable pH, on being superposed on the above profiles, it attests to a pH-independent mode of release.

EXAMPLE 5

Pharmacokinetic characteristics

FIG. 3 shows the mean curve for the plasma levels of 5-ISMN observed after administration to 3 subjects at a single dose of a tablet No. 2; the pharmacokinetic parameters calculated during this pilot screening study are as follows:

|  | Tmax h | Cmax ng · ml$^{-1}$ | T½ h | MRT h | AUC 0-∞ ng · ml$^{-1}$ · h |
|---|---|---|---|---|---|
| MEAN | 4.67 | 386.27 | 4.72 | 10.02 | 4670.33 |
| S.D | 1.53 | 35.44 | 2.06 | 1.46 | 470.08 |

On this mean plasma curve, taking into account the existence of a recorded minimal effective concentration value of 100 ng.ml$^{-1}$ (=$C_{eff}$), the maintenance of plasma levels above this value, without a significant latency time, during a time period t C $C_{eff}$ (sic) in the region of 16 hours, is noted.

EXAMPLE 6

In vivo absorption profile

FIG. 4 shows the mean curve for the percentages of 5-ISMN absorbed. The absorption profile obtained is characterized by a zero order entry up to approximately the fifth hour following administration; in consequence, the constant mean flux of in vivo absorption calculated from this curve is of the order of 13.37% $h^{-1}$.

We claim:

1. Sustained-release tablet, characterized in that it comprises as active principle, isosorbide 5-mononitrate (5-ISMN) in the form of a powder having the following particle size profile:
   40 to 60% of isosorbide 5-mononitrate of particle size larger than 80 μm and smaller than 100 μm,
   20 to 50% of isosorbide 5-mononitrate of particle size larger than 100 μm and smaller than 250 μm,
   approximately 5% of isosorbide 5-mononitrate of particle size larger than 250 μm and smaller than 500 μm,
   approximately 0.5% of isosorbide 5-mononitrate of particle size larger than 500 μm,
   approximately 0% to 34.5% of isosorbide 5-mononitrate having a particle size smaller than 80 μm,
   in a homogeneous dispersion in a hydrophilic matrix comprising at least one swelling agent and at least one diluent, at a swelling agent to diluent weight ratio of between 0.2 and 0.7, said swelling agent containing a hydrophilic polymeric substance of apparent viscosity between about 0.1 and 100 Pa.s.

2. Sustained-release tablet according to claim 1, characterized in that the powder is preferably an isosorbide 5-mononitrate powder in which at least 70% of the particles are between 80 μm and approximately 250 μm in size.

3. Sustained-release table according to claim 1 or 2, characterized in that the active principle is present in the proportion of 5 to 20% by weight, and preferably in the proportion of approximately 10% by weight, relative to the total weight of said tablet.

4. Sustained-release tablet according to claim 1, characterized in that the swelling agent and the diluent are present in the said tablet according to a swelling agent-/diluent ratio of between 0.2 and 0.7, and preferably equal to approximately 0.5.

5. Sustained-release table according to claim 4, characterized in that the swelling agent contains a hydrophilic polymeric substance of apparent viscosity between about 0.1 and 100 Pa.s.

6. Tablet according to claim 5, characterized in that the hydrophilic polymeric substance is chosen from the family of proteinaceous or cellulosic hydrocolloids, and preferably from alginic derivatives, natural gums, methylcellulose, carboxymethylcellulose, hydroxypropylcellulose and/or ethylhydroxypropylcellulose.

7. Sustained-release tablet according to claim 6, characterized in that the polymeric substance is preferably methylhydroxypropylcellulose of viscosity of about 15 Pa.s.

8. Sustained-release tablet according to claim 1 or 2, characterized in that the diluent contains at least one intrinsic diluent and one thickener.

9. Sustained-release tablet according to claim 8, characterized in that the thickener/-diluents ratio is between 0.1 and 0.6, and preferably equal to approximately 0.3.

10. Sustained-release tablet according to claim 9, characterized in that the intrinsic diluent is preferably chosen from lactose, sorbitol, mannitol, calcium phosphate or sulfate, colloidal silica and/or microcrystalline cellulose.

11. Sustained-release tablet according to claim 8 or 9, characterized in that the thickener is preferably chosen from starches, starch derivatives, xanthan gums, microfine cellulose and/or dextrins.

12. Sustained-release tablet according to claim 1 or 2, characterized in that it comprises, in addition, an aqueous film-coating based on cellulose derivatives.

13. Sustained-release tablet according to claim 1 or 2, characterized in that the tablet also comprises other additives chosen from lubricants or coloring substances.

14. Process for manufacturing a tablet according to claim 1 or 2, characterized in that the following are carried out:
   sieving of the various swelling agents and diluents and of the active principle,
   mixing of these components and the active principle,
   addition of a lubricant and, where appropriate, other additives to this mixture,
   tableting of the mixture thereby obtained and, where appropriate,
   film-coating of said tablet.

* * * * *

UNITED STATES PATENT AND TRADEMARK OFFICE
CERTIFICATE OF CORRECTION

PATENT NO. : 5,334,393
DATED : August 2, 1994
INVENTOR(S) : Bougaret et al.

It is certified that error appears in the above-indentified patent and that said Letters Patent is hereby corrected as shown below:

Column 2, line 34, delete [Preferably;] and insert —Preferably,—.

Column 5, line 42, delete [table] and insert —tablet—.

Column 6, line 3, delete [table] and insert —tablet—.

Signed and Sealed this

Third Day of January, 1995

Attest:

BRUCE LEHMAN

Attesting Officer

Commissioner of Patents and Trademarks